United States Patent [19]

Furukawa

[11] Patent Number: 4,504,662

[45] Date of Patent: Mar. 12, 1985

[54] ISOXAZOLOPYRIMIDINE DERIVATIVES

[75] Inventor: Yoshiyasu Furukawa, Takarazuka, Japan

[73] Assignee: Takeda Chemical Industries, Ltd., Osaka, Japan

[21] Appl. No.: 472,105

[22] Filed: Mar. 4, 1983

[30] Foreign Application Priority Data

Mar. 8, 1982 [JP] Japan ................... 57-36807

[51] Int. Cl.$^3$ ................ C07D 487/04; A61K 31/505
[52] U.S. Cl. .................................. 544/255
[58] Field of Search ................ 424/251; 544/255

[56] References Cited

U.S. PATENT DOCUMENTS

| | | | |
|---|---|---|---|
| 2,957,875 | 10/1960 | Lyttle et al. | 544/277 |
| 3,056,781 | 10/1962 | Papesch | 544/255 |
| 3,094,529 | 6/1963 | Klosa | 544/272 X |
| 3,114,751 | 12/1963 | Whetstone | 544/276 X |
| 3,536,711 | 10/1970 | Dunn et al. | 544/276 X |
| 3,959,280 | 5/1976 | Furukawa et al. | 544/255 |
| 4,052,391 | 10/1977 | Furukawa et al. | 544/255 |
| 4,129,654 | 12/1978 | Marumoto et al. | 425/251 |
| 4,202,975 | 5/1980 | Marumoto et al. | 544/255 |

FOREIGN PATENT DOCUMENTS 2248231  4/1974  Fed. Rep. of Germany ...... 544/255

OTHER PUBLICATIONS

Hirota et al., Chemical Abstracts, vol. 95, 150,597a (1981).

*Primary Examiner*—Donald G. Daus
*Assistant Examiner*—Diana G. Rivers
*Attorney, Agent, or Firm*—Wegner & Bretschneider

[57] ABSTRACT

Isoxazolo[3,4-d]pyrimidines of the formula

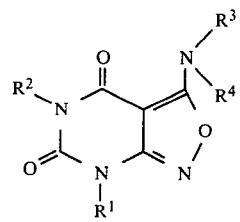

wherein $R^1$ and $R^2$, respectively, are lower alkyl; $R^3$ is lower alkyl or acyl; and $R^4$ is hydrogen, lower alkyl, or acyl have antiflammatory, analgesic and antipyretic activities in mammals and low acute and subacute toxicities, as well. The compounds are particularly useful as an antiinflammatory, analgesic and antipyretic drug.

8 Claims, No Drawings

ISOXAZOLOPYRIMIDINE DERIVATIVES

This invention relates to novel isoxazolopyrimidine derivatives which are of value as medicines, and the production thereof.

In more particular, the present invention relates to an isoxazolopyrimidine derivative of the formula:

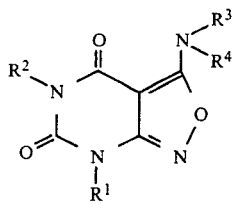

(I)

wherein $R^1$ and $R^2$, respectively, represent lower alkyl; $R^3$ is lower alkyl, or acyl; $R^4$ is hydrogen, lower alkyl, or acyl, and the production thereof.

With reference to the formula (I), the lower alkyl represented by $R^1$ or $R^2$ is alkyl of 1 to 3 carbon atoms such as methyl, ethyl, propyl and isopropyl, especially methyl or ethyl being preferable. Most preferred $R^1$ and $R^2$ are methyl, respectively.

The acyl designated by $R^3$ or $R^4$ is alkylcarbonyl, arylcarbonyl or 5 to 6-membered heterocycle-carbonyl, among these acyls, alkyl carbonyl being preferable.

As the alkylcarbonyl, there may be mentioned alkylcarbonyl whose alkyl moiety is straight-chain, branched or cyclic alkyl having 1 to 10 carbon atoms such as methyl, ethyl propyl, isopropyl, butyl, t-butyl, isobutyl, pentyl, cyclohexyl, octyl and decyl. The preferred alkylcarbonyl is alkylcarbonyl whose alkyl moiety is straight-chain or branched $C_{1-4}$ alkyl or alkylcarbonyl whose alkyl moiety is $C_{5-6}$ cyclic alkyl (cycloalkyl). As the aryl moiety of the arylcarbonyl, these may be mentioned phenyl which may be substituted by hydroxyl, $C_{1-4}$ alkyl (e.g., methyl, ethyl, isopropyl) and $C_{1-4}$ alkoxyl (e.g., methoxyl, ethoxyl, propoxyl, isopropoxyl). These substituents may be substituted on the position of o-, m- or p-position of the phenyl. As the heterocyclic moiety of the 5 or 6-menbered heterocyclecarbonyl, there may be mentioned, for example, thiophene, furan and pyridine.

As the lower alkyl designated by $R^3$ or $R^4$, there may be mentioned straight-chain or branched alkyl of 1 to 5 carbon atoms such as methyl, ethyl, propyl, isopropyl, butyl, t-butyl and isobutyl. Among these lower alkyl, lower alkyl of 1 to 3 carbon atoms is preferable. Among the aforesaid compounds (I), preferable is a compound wherein $R^1$ and $R^2$ are methyl, respectively; $R^3$ is acyl, particularly alkylcarbonyl whose alkyl moiety is straight-chain, branched or cyclic alkyl having 1 to 10 carbon atoms; and $R^4$ is hydrogen or acyl, particularly alkylcarbonyl as defined just above in $R^3$, hydrogen being more preferable.

The compound (I) of the present invention can be produced by subjecting a compound of the formula:

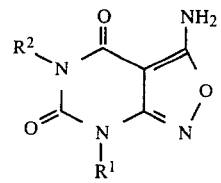

(II)

wherein $R^1$ and $R^2$ each are as defined hereinbefore to acylation and/or alkylation. More particularly, this invention provides a process for the production of a compound (I) which comprises reacting a compound (II) with a reactive derivative of a carboxylic acid and/or a lower alkyl halide.

Acylation is conducted by reacting a compound (II) with a reactive derivative of a carboxylic acid corresponding to the acyl as defined hereinbefore. As the reactive derivative, there may be mentioned acid halides such as $C_{1-10}$ alkylcarbonyl chloride (e.g. acetyl chloride, propionyl chloride, isobutyryl chloride, caproyl chloride, cyclohexanecarbonyl chloride), arylcarbonyl chloride (p-methylbenzoyl chloride, benzoyl chloride, o-methoxybenzoyl chloride, o-hydroxylbenzoyl chloride) and 5 or 6-membered heterocycle-carbonyl chloride (e.g. 2-furoyl chloride, 2-thiophene-carbonyl chloride) and acid anhydrides such as $C_{1-10}$ alkyl carboxylic acid anhydride (e.g., acetic anhydride, propionic anhydride). The reaction is normally carried out in an organic solvent. The examples of the solvent include carboxylic acid esters such as ethyl acetate and butyl acetate, ethers such as tetrahydrofuran and dioxane, and chlorinated hydrocarbons such as chloroform. Also, this reaction is normally carried out in the presence of a base. As the base, there may be mentioned organic amines such as tertiary alkylamines (e.g., triethylamine, tributylamine), pyridine and picoline, as well as alkali metal salts such as sodium hydrogencarbonate, potassium hydrogencarbonate, sodium carbonate and potassium carbonate, and the above pyridine and picoline can also be employed as a reaction solvent. The reaction temperature is normally in the range of about 0° to 150° C., and the reaction time ranges from several minutes to about 10 hours. By controlling the amount of the acylating agent, reaction temperature, reaction time, etc., mono- or di-acyl derivatives or a mixture thereof can be produced. Generally speaking, the reactive derivative of a carboxylic acid is used in an amount of about 1 to 10 moles to 1 mole of a compound [II] in the production of mono-acyl derivatives and in an amount of about 2 to 10 moles to 1 mole of a compound [II] in the production of di-acyl derivatives. Separation between mono- and di-acyl derivatives can be carried out by known procedures such as chromatography and recrystalization. Diacyl derivatives can advantageously be produced by acylating a monoacyl derivative with a $C_{1-10}$ alkylcarbonyl chloride as described above. This reaction is normally carried out in an organic solvent such as chlorinated hydrocarbons (e.g. chloroform and dichloromethane) in the presence of a base such as trialkylamine (e.g. triethylamine and tributylamine). The reaction temperature is normally in the range of about 0° to 100° C. and the reaction time ranges from several minutes to about 1 hour.

Alkylation is conducted by reacting a lower $C_{1-5}$ alkyl halide (e.g., propyl bromide, methyl iodide, ethyl iodide, isopropyl iodide, butyl iodide) with a compound (II). The reaction is normally carried out in an organic solvent. The examples of the solvent include carboxylic acid esters such as ethyl acetate; ethers such as tetrahydrofuran and dioxane; dimethylformamide, diethylformamide, dimethylacetamide, diethylacetamide, dimethylsulfoxide, and so forth. Also, this reaction is normally carried out in the presence of a base. The examples of the base which are employable include organic tertiary amines such as triethylamine and tributylamine, alkali metal salts such as potassium carbonate, sodium carbonate, sodium hydrogencarbonate and potassium hydrogencarbonate, and others. The reaction temperature is normally in the range of about 0° to 150° C., and the reaction time ranges from several minutes to about 10 hours. By controlling the amount of the alkylating agent, reaction temperature and reaction time, mono- or di-alkyl derivative, or a mixture thereof can be produced. Generally speaking, the lower alkyl halide is used in an amount of about 1 to 10 moles to 1 mole of a compound [II] in the production of mono-alkyl derivatives and in an amount of about 2 to 10 moles to 1 mole of a compound [II] in the production of di-alkyl derivatives. Separation between mono- and di-alkyl derivatives can be carried out by known procedures such as chromatography and recrystalization.

When acylation and alkylation are consecutively conducted, the order is not critical, and either of them may be first conducted. Also, the mono-acylated or mono-alkylated derivative formed in the first reaction may be subjected to the subsequent reaction without being isolated. Acylation of the mono-alkyl derivative and alkylation of the mono-acyl derivative are both carried out according to the above-mentioned conditions, respectively, and the objective alkyl-acyl derivatives are thus obtained.

The contemplated isoxazolopyrimidine compounds (I) exhibit antiinflammatory, analgesic and anti-pyretic activities in mammals. In addition to this, the compounds [I], especially those having methyl as $R^1$ and $R^2$, acyl as $R^3$ and hydrogen as $R^4$, have low toxicity (e.g. acute and subacute toxicity). Particularly the mono-acyl compounds have lower subacute toxicity to viscera such as heart, liver, kidneys, thymus, spleen, adrenals, lung and testes. Furthermore, the compounds [I] possess no ulcerogenic activity. Therefore, the compounds of the present invention are of value, for example, as medicines for the amelioration and management of headache, tooth ache, neuralgia, lumbago, bursitis, rheumatoid arthritis, etc. In cases in which the compounds (I) are employed as such medicines, they can be safely administered orally or parenterally, either as they are in bulk form or in the dosage forms such as powder, granule, tablet, capsule, injection, suppository or ointment as prepared by mixing with a pharmacologically acceptable carrier, excipient or diluent. The dosage, at which the compounds (I) are, for example, administered orally for the treatment of arthritis, lumbago and bursiti in adult humans, is desirably in the range of about 0.1 to about 30 mg/kg (body weight), preferably about 0.5 to about 6 mg/kg (body weight).

The starting compound (II), which is used in the preparation of the compounds (I) of the present invention, can be produced for example by reacting a compound of the formula:

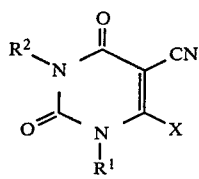

(III)

[wherein X is a halogen atom (e.g., chlorine, bromine); other symbols are as defined hereinbefore] with hydroxylamine in the presence of a base.

Hydroxylamine is normally used in the form of the acid addition salt exemplified by the hydrochloride salt hydrobromide salt and sulfate salt. The base may be exemplified by weak bases such as sodium acetate, potassium acetate and sodium hydrogencarbonate, and the object compound (II) can be obtained in a high yield normally by carrying out the reaction in alcohol such as methanol, ethanol and propanol at room temperature or under cooling.

The Reference Examples, Examples and Experiment Examples are described in the following to illustrate the present invention more specifically, but are not intended to limit the scope of the present invention.

REFERENCE EXAMPLE 1

3-Amino-5,7-dimethyl-isoxazolo[3,4-d]pyrimidine-4,6-(5H,7H)-dione.

1.4 g of 6-chloro-5-cyano-1,3-dimethyluracil was stirred together with a mixture of 150 ml of methanol, 6.0 g of sodium acetate trihydrate and 3.0 g of hydroxylamine hydrochloride at room temperature for 3 hours. Resulting precipitates were recovered by filtration and washed with 10 ml of water twice and then with 5 ml of methanol. The precipitates were recrystallized from dimethylformamide-water to give 1.2 g of light yellow prisms, melting point: 280°–284° C. (decomp.). Ultraviolet absorption spectrum: $\lambda_{max}{}^{H2O}$ 266 nm ($\epsilon = 8780$)

Elemental analysis, for $C_7H_8N_4O_3$; Calcd. C, 42.85; H, 4.10; N, 28.56; Found C, 42.90; H, 4.39; N, 28.43.

REFERENCE EXAMPLE 2

The following compound was prepared in a similar manner to that of Reference Example 1.

3-Amino-5,7-diethyl-isoxazolo[3,4-d]pyrimidine-4,6-(5H,7H)-dione (melting point: 193°–194° C.).

EXAMPLE 1

5,7-Dimethyl-3-propionylamino-isoxazolo[3,4-d]pyrimidine-4,6(5H,7H)-dione.

2.88 g of 3-amino-5,7-dimethyl-isoxazolo[3,4-d]pyrimidine-4,6(5H,7H)-dione was dissolved in 100 ml of pyridine under heating, and 5.07 g of propionic anhydride was added to the solution, followed by stirring at 100° C. for 2.5 hours. The solvent was removed from the reaction solution under reduced pressure, and the residue was recrystallized from isopropyl ether-acetone to give 2.60 g of colorless prisms, melting point: 150°–152° C.

EXAMPLE 2

5,7-Dimethyl-3-propionylamino-isoxazolo[3,4-d]pyrimidine-4,6(5H,7H)-dione.

0.588 g of 3-amino-5,7-dimethyl-isoxazolo[3,4-d]pyrimidine-4,6(5H,7H)-dione was dissolved in 15 ml of pyridine under heating. Then, 1.5 g of propionyl chloride was added to the solution, and the mixture was stirred at 80° C. for 4 hours. The solvent was removed from the reaction solution under reduced pressure. To the residue was added water, which was subjected to extraction with chloroform. The chloroform layer was taken and dried over anhydrous sodium sulfate and evaporated to dryness. The residue was chromatographed on a column of silica gel, and the column was eluted with chloroform:acetone:formic acid (20:1:0.1). The intended compound was recovered from the resultant eluate and recrystallized from isopropyl ether-acetone to give 0.345 g of colorless prisms, melting point: 150°–152° C.

EXAMPLE 3

3-Cyclohexylcarbonylamino-5,7-dimethylisoxazolo[3,4-d]pyrimidine-4,6(5H,7H)-dione.

To a solution of 17.5 g of 3-amino-5,7-dimethylisoxazolo[3,4-d]pyrimidine-4,6(5H,7H)-dione in 350 ml of pyridine, 26.2 g of cyclohexanecarbonyl chloride was added and the mixture was heated at 50° C. for 3 hours. The mixture was evaporated to dryness under reduced pressure and 200 ml of methanol was added to the residue. The resultant crystals were recrystallized twice from chloroform-methanol to afford 15.7 g of colorless needles, m.p. 210°–212° C.

EXAMPLE 4

The following compounds were prepared in a similar manner to that of Example 1, 2 or 3.

(i) 3-Acetylamino-5,7-dimethyl-isoxazolo[3,4-d]pyrimidine-4,6-(5H,7H)-dione (melting point: 191°–192° C.), (ii) 3-Butyrylamino-5,7-dimethyl-isoxazolo[3,4-d]pyrimidine-4,6(5H,7H)-dione (melting point: 88°–89° C.), (iii) 5,7-Dimethyl-3-isovalerylamino-isoxazolo[3,4-d]pyrimidine-4,6(5H,7H)-dione (melting point: 173°–175° C.), (iv) 5,7-Dimethyl-3-isobutyrylamino-isoxazolo[3,4-d]pyrimidine-4,6(5H,7H)-dione (melting point: 177°–178° C.), (v) 3-Caprylamino-5,7-dimethyl-isoxazolo[3,4-d]pyrimidine-4,6(5H,7H)-dione; (melting point: 108°–110° C.), (vi) 3-Benzoylamino-5,7-dimethyl-isoxazolo[3,4-d]pyrimidine-4,6(5H,7H)-dione (melting point: 198°–200° C.), (vii) 5,7-Dimethyl-3-(p-methylbenzoyl)amino-isoxazolo[3,4-d]pyrimidine-4,6(5H,7H)-dione (melting point: 228°–230° C.), (viii) 5,7-Dimethyl-3-(o-methoxybenzoyl)aminoisoxazolo[3,4-d]pyrimidine-4,6(5H,7H)-dione (melting point: 270°–274° C. (decomp.)), (ix) 5,7-Dimethyl-3-(2-furoyl)amino-isoxazolo[3,4-d]pyrimidine-4,6(5H,7H)-dione (melting point: 230°–233° C.), (x) 5,7-Dimethyl-3-(o-hydroxybenzoyl)amino-isoxazolo[3,4-d]pyrimidine-4,6(5H,7H)-dione (melting point: >300° C.) and (xi) 5,7-Diethyl-3-propionylamino-isoxazolo[3,4-d]pyrmidine-4,6(5H,7H)-dione (melting point: 141°–142° C.).

EXAMPLE 5

5,7-Dimethyl-3-N,N-dipropionylamino-isoxazolo[3,4-d]pyrimidine-4,6(5H,7H)-dione.

To a suspension of 1 g of 3-amino-5,7-dimethyl-isoxazolo[3,4-d]pyrimidine-4,6(5H,7H)-dione in 30 ml of chloroform, 1 g of triethylamine and 1.5 g of propionic anhydride were added and the mixture was refluxed for 1.5 hours. The mixture was evaporated to dryness under reduced pressure and the residue was put on a column of 30 g of silica gel, and the column was eluted with chloroform. The first fractions were pooled and evaporated to dryness and the residue was crystallized from ether-hexane to afford 0.1 g of colorless needles. m.p. 117°–119° C.

EXAMPLE 6

3-(N-acetyl-N-propionyl)amino-5,7-dimethylisoxazolo[3,4-d]pyrimidine-4,6(5H,7H)-dione To a solution of 2 g of 5,7-dimethyl-3-propionylamino-isoxazolo[3,4-d]pyrimidine-4,6(5H,7H)-dione in 80 ml of chloroform, 0.8 g of triethylamine and 0.625 g of acetyl chloride were added. The mixture was stirred at room temperature for 30 minutes and evaporated to dryness under reduced pressure. The residue was put on a column of 30 g of silica gel and the column was eluted with chloroform. Fractions contains the objective compound were pooled and evaporated to dryness under reduced pressure. The residue was crystallized from ether-hexane to afford 1.3 g of colorless prisms, m.p. 92°–94° C.

EXAMPLE 7

The following compounds were prepared in a similar manner to that of Examples 5 or 6.

(i) 5,7-Diethyl-3-N,N-dipropionylamino-isoxazolo[4,3-d]pyrimidine-4,6(5H,7H)-dione (melting point: 113°–114° C.), (ii) 5,7-Dimethyl-3-N,N-di-(p-methylbenzoyl)amino-isoxazolo[3,4-d]pyrimidine-4,6(5H,7H)-dione (melting point: 168°–170° C.), (iii) 5,7-Dimethyl-3-N,N-di-(2-thiophenecarbonyl)amino-isoxazolo[3,4-d]pyrimidine-4,6-dione (melting point: 150°–152° C.), (iv) 5,7-Dimethyl-3-N,N-dipropionylamino-isoxazolo[3,4-d]pyrimidine-4,6(5H,7H)-dione (melting point: 117°–119° C.), and (v) 3-N,N-diacetylamino-5,7-dimethyl-isoxazolo[3,4-d]pyrimidine-4,6(5H,7H)-dione (melting point: 130°–133° C.).

EXAMPLE 8

5,7-Dimethyl-3-propylamino-isoxazolo[3,4-d]pyrimidine-4,6(5H,7H)-dione.

A mixture of 0.588 g of 3-amino-5,7-dimethyl-isoxazolo[3,4-d]pyrimidine-4,6(5H,7H)-dione, 15 ml of dimethylformamide, 2.5 g of propyl iodide and 1.0 g of potassium carbonate was stirred at 100° C. for 3 hours. From the reaction solution was removed the solvent under reduced pressure. To the residue was added water, which was subjected to extraction with chloroform. The chloroform layer was taken and dried over anhydrous sodium sulfate, from which was removed the solvent. The resultant residue was chromatographed on a column of silica gel (30 g), and the column was eluted with chloroform:acetone:formic acid (20:1:0.1). From the elute was recovered the desired compound, which was recrystallized from isopropyl ether-acetone to give 0.217 g of colorless prisms, melting point: 164°–166° C.

EXAMPLE 9

The following compounds were prepared in a similar manner to that of Example 8.

(i) 5,7-Dimethyl-3-ethylamino-isoxazolo[3,4-d]pyrimidine-4,6(5H,7H)-dione (melting point: 184°–186° C.), (ii) 5,7-Dimethyl-3-iso-propylamino-isoxazolo[3,4-d]pyrimidine-4,6(5H,7H)-dione (melting point: 194°–196° C.), (iii) 3-Isobutylamino-5,7-dimethyl-isoxazolo[3,4-d]pyrimidine-4,6(5H,7H)-dione (melting point: 182°–183° C.), and (iv) 3-Butylamino-5,7-dimethyl-isoxazolo[3,4-d]pyrimidine-4,6(5H,7H)-dione (melting point: 152°–153° C.).

EXAMPLE 10

5,7-Dimethyl-3-dimethylamino-isoxazolo[3,4-d]pyrimidine-4,6(5H,7H)-dione.

A mixture of 1.0 g of 3-amino-5,7-dimethyl-isoxazolo[3,4-d]pyrimidine-4,6(5H,7H)-dione, 5.0 g of methyl iodide, 40 ml of dimethylacetamide and 2.4 g of potassium carbonate was stirred at 40° C. for 3 hours. From the reaction solution was removed the solvent under reduced pressure. To the residue was added water, which was subjected to extraction with chloroform. The chloroform extract was taken and dried over anhydrous sodium sulfate. From the solution was removed the solvent. The residue was recrystallized from isopropyl ether-acetone to yield 0.40 g of colorless needles, melting point: 188°–190° C.

EXAMPLE 11

The following compounds were prepared in a similar manner to that of Example 10.

(i) 5,7-Dimethyl-3-dipropylamino-isoxazolo[3,4-d]pyrimidine-4,6(5H,7H)-dione (melting point: 76°–77° C.), (ii) 3-Diethylamino-5,7-dimethyl-isoxazolo[3,4-d]pyrimidine-4,6(5H,7H)-dione (melting point: 98°–100° C.), and (iii) 3-Dibutylamino-5,7-dimethyl-isoxazolo[3,4-d]pyrimidine-4,6(5H,7H)-dione [oily substance; nuclear magnetic resonance spectrum (deuterochloroform) ppm: 0.93(6H, triplet), 0.8–2.0(8H,multiplet), 3.30 and 3.37(3H each, singlet), 3.53–4.0(4H, multiplet)].

EXAMPLE 12

3-(N-acetyl-N-propyl)amino-5,7-dimethyl-isoxazolo[3,4-d]pyrimidine-4,6(5H,7H)-dione.

A mixture of 0.21 g of 5,7-dimethyl-3-propylamino-isoxazolo[3,4-d]pyrimidine-4,6(5H,7H)-dione, 4 ml of acetyl chloride and 4 ml of pyridine was stirred at 50° C. for 3 hours. Then, the solvent was distilled off under reduced pressure to leave a residue. The residue was chromatographed on a column of silica gel, and elution was performed with chloroform. The intended compound was recovered from the resultant eluate and recrystallized from isopropyl ether to yield 0.11 g of colorless needles, melting point: 85°–87° C.

EXAMPLE 13

The following compounds were prepared in a similar manner to that of Example 12.

(i) 3-(N-acetyl-N-isopropyl)amino-5,7-dimethyl-isoxazolo[3,4-d]pyrimidine-4,6(5H,7H)-dione (melting point: 90°–91° C.), and (ii) 5,7-Dimethyl-3-(N-propionyl-N-propyl)amino-isoxazolo[3,4-d]pyrimidine-4,6(5H,7H)-dione (oily substance: nuclear magnetic resonance spectrum (deuterochloroform) ppm: 0.88(3H, triplet, J=7 Hz), 1.13(3H, triplet, J=7 Hz), 1.4–2.0(2H, multiplet), 2.40(2H, quartet, J=7 Hz), 3.36 and 3.48(3H each, singlet), 3.96(2H, triplet, J=7 Hz).

EXAMPLE 14

5,7-Dimethyl-3-(N-propionyl-N-ethyl)amino-isoxazolo[3,4-d]pyrimidine-4,6(5H,7H)-dione.

A mixture of 0.187 g of 5,7-dimethyl-3-propionylamino-isoxazolo[3,4-d]pyrimidine-4,6(5H,7H)-dione, 9 ml of N,N-dimethylacetamide, 0.69 g of potassium carbonate and 0.62 g of ethyl iodide was stirred at 60° C. for 12 hours. From the reaction solution was removed the solvent under reduced pressure, and the residue was subjected to extraction with chloroform. The chloroform layer was washed with water, dried over anhydrous sodium sulfate. From the solution was removed the solvent to give 0.182 g of an oily substance. Nuclear magnetic resonance spectrum (deuterochloroform): ppm: 1.15 and 1.18(3H each, triplet, J=7 Hz), 2.43(2H, quartet, J=7 Hz), 3.36 and 3.50(3H each, singlet), 4.03(2H, quartet, J=7 Hz).

EXAMPLE 15

The following compounds were prepared in a similar manner to that of Example 14.

(i) 3-(N-acetyl-N-methyl)amino-5,7-dimethyl-isoxazolo[3,4-d]pyrimidine-4,6(5H,7H)-dione (melting point: 83°–85° C.), (ii) 3-(N-acetyl-N-ethyl)amino-5,7-dimethyl-isoxazolo[3,4-d]pyrimidine-4,6(5H,7H)-dione (melting point: 99°–100° C.), and (iii) 5,7-Dimethyl-3-(N-methyl-N-propionyl)amino-isoxazolo[3,4-d]pyrimidine-4,6(5H,7H)-dione (melting point: 108°–110° C.).

EXPERIMENT EXAMPLE 1

Antiinflammatory action (Carrageenin-induced edema method)

With use of Jcl:SD rats (male, of body weight ranging from 180 to 220 g) divided into groups each consisting of 6 rats, the antiinflammatory action was measured according to the method of Winter et al.[1]. One hour after oral administration of a test compound, each was injected subcutaneously with 0.05 ml of a 1% solution of carrageenin in isotonic saline solution into the right paw. The volume of the hind-limb before carrageenin injection and 3 hours thereafter was measured, respectively. The volume of edema was determined based on the difference between the volumes. The suppression of edema was determined by comparing the non-treated as treated groups in the volume of edema.

[1]Winter, C. A., Risley, E. A. and Nuss, G. W., Proc. Soc. exp. Biol. Med. 111, 544 (1962).

Compound 1: 5,7-Dimethyl-3-propionylamino-isoxazolo[3,4-d]pyrimidine-4,6(5H,7H)-dione Compound 2: 5,7-Dimethyl-3-(N-propionyl-N-propyl)amino-isoxazolo[3,4-d]pyrimidine-4,6(5H,7H)-dione Compound 3: 3-Cyclohexylcarbonylamino-5,7-dimethyl-isoxazolo[3,4-d]pyrimidine-4,6(5H,7H)-dione The results are set forth in Table 1.

TABLE 1

| Exp. No. | Test compound | Oral Dosage mg/kg | Average volume of edema ml ± S.E. | Suppression % |
|---|---|---|---|---|
| 1 | Control | — | 0.468 ± 0.026 | — |
| 2 | Control | — | 0.545 ± 0.033 | — |

TABLE 1-continued

| Exp. No. | Test compound | Oral Dosage mg/kg | Average volume of edema ml ± S.E. | Suppression % |
|---|---|---|---|---|
| 1 | Compound 1 | 12.5 | 0.272 ± 0.031** | 42.0 |
| 2 | Compound 1 | 50 | 0.112 ± 0.022** | 79.5 |
| 3 | Control | — | 0.597 ± 0.049 | — |
| 4 | Control | — | 0.577 ± 0.054 | — |
| 3 | Compound 2 | 12.5 | 0.320 ± 0.041** | 46.4 |
| 4 | Compound 2 | 50 | 0.282 ± 0.032** | 51.1 |
| 5 | Control | — | 0.515 ± 0.023 | — |
| 6 | Control | — | 0.535 ± 0.036 | — |
| 5 | Compound 3 | 12.5 | 0.360 ± 0.028** | 29.7 |
| 6 | Compound 3 | 50 | 0.190 ± 0.020** | 64.5 |

**$P < 0.01$, as compared with control.

EXPERIMENT EXAMPLE 2

Analgesic action (Phenylquinone-writhing method)

With use of Slc:ICR mice (male, of body weight ranging from 18 to 23 g) divided into groups each consisting of 10 mice, the analgesic action was examined according to the method of Siegmund et al.[2]. 30 minutes after oral administration of a test compound, each mouse was injected intraperitoneally with a 0.02% aqueous phenylquinone solution at the ratio of 0.1 ml per 10 g of body weight. The number of writhings was counted over the period of 20 minutes thereafter. The suppression of writhing was determined by comparing the response numbers of the nontreated as those of treated groups.

(2): Siegmund, E, Cadmus, R. and Lu, G., Proc. Soc. exp. Biol. Med., 95, 729 (1957).

The results are set forth in Table 2.

TABLE 2

| Exp. No. | Test compound | Dosage (oral) mg/kg | Average number of writhings ± S.E. | Suppression % |
|---|---|---|---|---|
| 1 | Control | — | 9.5 ± 1.9 | — |
| 2 | Control | — | 14.7 ± 2.8 | — |
| 1 | Compound 1 | 25 | 3.2 ± 0.9* | 66.3 |
| 2 | Compound 1 | 50 | 4.5 ± 1.5* | 69.4 |
| 3 | Control | — | 14.7 ± 2.8 | — |
| 4 | Control | — | 14.7 ± 2.9 | — |
| 3 | Compound 2 | 3.13 | 1.7 ± 1.3** | 88.2 |
| 4 | Compound 2 | 6.25 | 0.9 ± 0.4** | 93.9 |

*$P < 0.05$
**$P < 0.01$ as compared with control.

EXPERIMENT EXAMPLE 3

The acute toxicity data for some representative isoxazolo[3,4-d]pyrimidines are given below.

| Test Compound | | | | | Oral Dosage | Mortality |
|---|---|---|---|---|---|---|
| $R^1$ | $R^2$ | $R^3$ | $R^4$ | Animals | (mg/kg) | |
| $CH_3$ | $CH_3$ | $COC_2H_5$ | H | rat | 500 | 0/6 |
| | | | | mouse | 500 | 0/5 |
| $CH_3$ | $CH_3$ | CO—⟨H⟩ | H | rat | 500 | 0/6 |
| | | | | mouse | 500 | 0/5 |
| $CH_3$ | $CH_3$ | $COC_2H_5$ | $COC_2H_5$ | rat | 500 | 0/6 |
| | | | | mouse | 500 | 0/5 |

EXPERIMENT EXAMPLE 4

The subacute toxicity data for some representative isoxazolo[3,4-d]pyrimidines are given below.

Animals: rat

Oral Dosage: 200 mg/kg/day for two weeks

| Test Compound | | | | Hemosiderin deposition at spleen number of animals | | | | |
|---|---|---|---|---|---|---|---|---|
| $R^1$ | $R^2$ | $R^3$ | $R^4$ | 1 | 2 | 3 | 4 | 5 |
| $CH_3$ | $CH_3$ | $COC_2H_5$ | H | ± | − | + | + | + |
| $CH_3$ | $CH_3$ | CO—⟨H⟩ | H | ± | ± | ± | ± | ± |
| Control (without test compound) | | | | ± | − | ± | ± | ± |

−: no deposition; ±: very slight deposition;
+: slight deposition (by a microscopic observation)

What is claimed is:

1. A compound of the formula wherein
$R^1$ and $R^2$ are methyl;
$R^3$ is alkylcarbonyl in which the alkyl moiety is straight-chain, branched or cyclic alkyl having 1 to 10 carbon atoms, phenylcarbonyl which may be substituted by hydroxyl, $C_{1-4}$alkyl or $C_{1-4}$alkoxyl, or 5- or 6-membered heterocycle-carbonyl selected from thiophenecarbonyl, furancarbonyl and pyridinecarbonyl; and
$R^4$ is hydrogen, alkylcarbonyl in which the alkyl moiety is straight-chain, branched or cyclic alkyl having 1 to 10 carbon atoms, phenylcarbonyl which may be substituted by hydroxyl, $C_{1-4}$alkyl or $C_{1-4}$alkoxyl, or 5- or 6-membered heterocycle-carbonyl selected from thiophenecarbonyl, furancarbonyl and pyridinecarbonyl.

2. A compound according to claim 1 wherein $R^3$ is alkylcarbonyl in which the alkyl moiety is straight-chain, branched or cyclic alkyl having 1 to 10 carbon atoms and $R^4$ is alkylcarbonyl as defined in $R^3$.

3. A compound according to claim 1, wherein $R^1$ and $R^2$ are methyl, respectively; $R^3$ is alkylcarbonyl in which the alkyl moiety is straight-chain, branched or cyclic alkyl having 1 to 10 carbon atoms, phenylcarbonyl which may be substituted by hydroxyl, $C_{1-4}$alkyl or $C_{1-4}$alkoxyl, or 5- or 6-membered heterocycle-carbonyl selected from thiophenecarbonyl, furancarbonyl and pyridinecarbonyl; and $R^4$ is hydrogen.

4. A compound according to claim 3, wherein the acyl designated by $R^3$ is alkylcarbonyl in which the alkyl moiety is straight-chain, branched or cyclic alkyl having 1 to 10 carbon atoms.

5. A compound according to claim 4, wherein the alkylcarbonyl is alkylcarbonyl in which the alkyl moiety is straight-chain or branched $C_{1-4}$ alkyl or alkycarbonyl whose alkyl moiety is $C_{5-6}$ cyclic alkyl.

6. A compound according to claim 1, wherein the compound is 5,7-dimethyl-3-propionylamino-isoxazolo[3,4-d]pyrimidine-4,6(5H,7H)-dione.

7. A compound according to claim 1, wherein the compound is 5,7-dimethyl-3-N,N-dipropionylamino-isoxazolo[3,4-d]pyrimidine-4,6(5H,7H)-dione.

8. A compound according to claim 1, wherein the compound is 3-cyclohexylcarbonylamino-5,7-dimethyl-isoxazolo[3,4-d]pyrimidine-4,6(5H,7H)-dione.

* * * * *